United States Patent

Passedouet et al.

[11] 4,015,013
[45] Mar. 29, 1977

[54] CERTAIN QUATERNARY AMMONIUM SALTS USED TO CONTROL GRAM-NEGATIVE BACTERIA

[75] Inventors: André Henri Passedouet, Maisons-Laffite; Robert Pipon, Melle, both of France

[73] Assignee: Rhone-Poulenc S.A., Paris, France

[22] Filed: June 10, 1975

[21] Appl. No.: 585,755

Related U.S. Application Data

[63] Continuation of Ser. No. 406,024, Oct. 12, 1973, abandoned.

[30] Foreign Application Priority Data

Oct. 16, 1972  France .................... 72.36571

[52] U.S. Cl. .................... 424/324; 260/458 C; 260/459 R; 260/562 N; 424/329
[51] Int. Cl.² .................... A01N 9/20; A01L 13/00
[58] Field of Search .................... 424/329, 324; 260/562 N

[56] References Cited

UNITED STATES PATENTS 3,014,046  12/1961  Speziale .................... 260/347.3

FOREIGN PATENTS OR APPLICATIONS 837,532  4/1952  Germany .................... 260/562

OTHER PUBLICATIONS

"Microbiology", Pelczar et al., pp. 232–233, 1958.

*Primary Examiner*—Leonard Schenkman
*Attorney, Agent, or Firm*—Stevens, Davis, Miller & Mosher

[57] ABSTRACT

Quaternary ammonium salts of the formula:

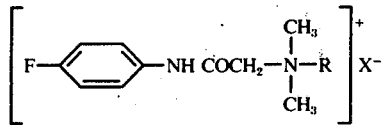

in which R is alkyl of 7 to 16 carbon atoms and $X^-$ is a monovalent anion, have interesting germicidal properties, especially against Gram-negative bacteria.

13 Claims, No Drawings

CERTAIN QUATERNARY AMMONIUM SALTS USED TO CONTROL GRAM-NEGATIVE BACTERIA

This application is a continuation of our application Ser. No. 406,024 filed Oct. 12, 1973 and now abandoned.

The present invention relates to quaternary ammonium salts which possess disinfectant properties, to their preparation, and to the disinfectant compositions for general and therapeutic use containing them.

Quaternary ammonium salts which carry one or two alkyl radicals containing at least 8 carbon atoms bonded to the nitrogen atom possess disinfectant properties. Amongst these quaternary ammonium salts, lauryldimethylbenzylammonium chloride, or benzalkonium chloride, is active against a large number of different kinds of germ. However, this compound is much less active, as a bactericide, against Gram-negative bacteria than against Gram-positive bacteria, which leads to its use only at concentrations sufficiently high to control the most resistant bacteria, in order to avoid simply limiting bacterial growth to the latter. An example of such resistant bacteria is *Pseudomonas aeruginosa* or *Bacillus pyocyaneus* which is responsible for numerous cases of infection in surgical and medical practice and even of whole working areas, which leads to their closure for disinfection.

The present invention provides novel quaternary ammonium salts of the formula:

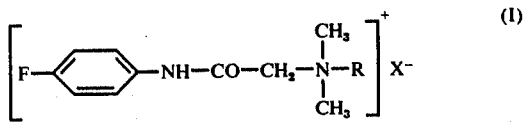

(I)

in which R is straight or branched alkyl of 7 to 16 carbon atoms, and $X^-$ is a monovalent anion of an inorganic or organic acid known to form quaternary ammonium salts.

The symbol R preferably represents n-heptyl, n-octyl, n-decyl, n-dodecyl, n-tetradecyl, n-hexadecyl, or 2-ethyl-hexyl, or a radical containing one or more methyl groups in which the total number of carbon atoms is between 7 and 16 and the radical corresponds to the alkyl part of alcohols containing 7 to 16 carbon atom each produced by the oxo synthesis from petroleum olefines. A preferred class of compounds of the invention consists of the compounds of formula (I) in which R is straight chain alkyl of 8 to 14 carbon atoms.

The nature of the anion $X^-$ is immaterial; however, the solubility in water of the compounds of formula (I) varies according to the nature of the anion. Generally, chlorides are more soluble than bromides and methosulphates while iodides and nitrates are insoluble or practically insoluble. Generally, chlorides are suitable for most uses.

According to the invention, the compounds of formula (I) are prepared by one of the following processes:

1. When, in the general formula (I), the anion $X^-$ is a halide ion, a 4-fluoro-carbanilinomethane of the formula:

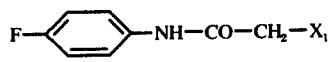

(II)

is reacted with a compound of the formula:

$$X_2-CH_3 \quad \text{(III)}$$

in which one of $X_1$ and $X_2$ is a halogen atom and the other is $N(CH_3)R$ in which R is as defined above.

The reaction is generally carried out in a organic solvent which is inert under the working conditions, such as a ketone, especially acetone or methyl ethyl ketone, or an ether such as butyl ether, and at a temperature of between about 20° C nd the reflux temperature of the reaction mixture. It is also possible to work in the absence of a solvent, at a temperature of between 20° and 120° C.

The compounds of formula (II) in which $X_1$ represents a halogen atom can be produced by reacting a halogenoacetyl halide with 4-fluoro-aniline.

The compounds of formula (III) in which $X_2$ represents $N(CH_3)$ R as defined above can be prepared by one of the following methods:

a. By reacting formaldehyde and formic acid with an amine of the general formula:

$$R-NH_2 \quad \text{(IV)}$$

in which R is as defined above, b. by methylation, by known methods, of an amine of the formula:

$$R-NH-CH_3 \quad \text{(V)}$$

in which R is as defined above. Such amine of formula (V) may be prepared by reacting methylamine with an alkyl halide of the formula:

$$R-Hal \quad \text{(VI)}$$

in which R is as defined above and Hal represents a halogen atom, or by reacting methylamine with an aldehyde of the formula:

$$R'-CHO \quad \text{(VII)}$$

in which R' represents an alkyl radical such that $R'-CH_2-$ represents the alkyl radical R as defined above.

The compounds of formula (II) in which $X_1$ represents a radical $N(CH_3)R$ as defined above, can be prepared by reacting an amine of formula (V) in which R is as defined above, with a compound of formula (II) in which $X_1$ represents a halogen atom.

2. When, in the general formula (I), the anion $X^-$ is other than a chloride ion, a metal salt of an inorganic or organic acid, other than a chloride is reacted in water with a compound of formula (I) in which $X^-$ is the chloride ion. A sodium salt dissolved in water, e.g. a bromide, iodide or nitrate, is generally used.

3. An alkyl ester of the general formula:

$$R-X \quad \text{(VIII)}$$

in which R is as defined above and X is a monovalent radical corresponding to the anion $X^-$, is reacted with the compound of formula:

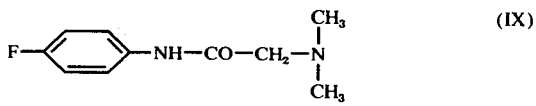

$$\text{(IX)}$$

which can itself be prepared by reacting dimethylamine with a compound of formula (II) in which $X_1$ represents a halogen atom.

The following Examples illustrate the invention.

EXAMPLE 1

A mixture of 4-fluoro-carbanilinochloromethane (39.55 g.), N,N-dimethylheptylamine (51.85 g.) and methyl ethyl ketone (60 cc.) is heated at 100° C, with stirring, for 15 minutes. The solid material, which has set solid during the heating, is broken up in the solvent and then filtered off and dried at 45° C under reduced pressue. (4-Fluoro-carbanilino-methyl)-heptyl-dimethylammonium chloride (82 g.) is thus obtained as a white powder which melts at 115° C.

4-Fluoro-carbanilino-chloromethane, used as the starting material, can be prepared in the following way: Chloroacetyl chloride (140.5 g.) is added, over the course of 2 hours and with stirring, to a mixture of 4-fluoro-aniline (120 g.), triethylamine (120 g.) and benzene (1,150 cc.) and kept at 30°–35° C. After the end of the addition, the reaction mixture is kept at 30°–35° C for 1 hour and then cooled to approximately 20° C; after adding water (300 cc.), the suspension obtained is stirred vigorously for 15 minutes. The solid remaining in suspension is filtered of, washed successively with water (250 cc.) and then with benzene (250 cc.), and dried at 50°–55° C under reduced pressure. 4-Fluorocarbanilino-chloromethane (168 g.) is thus obtained.

It is also possible to prepare this compound by reacting chloroacetyl chloride with 4-fluoroaniline in dichloroethane.

N,N-Dimethylheptylamine, also used as a starting material, can be prepared in the following way: N-Heptylamine (230 g.) is added slowly, with stirring and cooling, to formic acid (460 g.). A commercial aqueous solution of formaldehyde (580 cc.) is added, still with stirring, to the solution obtained; the mixture obtained is heated gradually. At about 60° C, carbon dioxide begins to be evolved; the temperature of the reaction mixture is gradually raised to 90° C and the mixture is kept at this temperature for 1½ hours, that is to say 15 minutes after the end of evolution of gas. After cooling, the reaction mixture is neutralised by adding sodium hydroxide pellets (250 g.), whilst the temperature is kept below 45° C. The organic phase is isolated, washed twice with water (a total of 100 cc.), dried, and then distilled under reduced pressure.

N,N-Dimethylheptylamine (180 g.) (boiling point = 77° C/25 mm.Hg.) is thus obtained.

EXAMPLE 2

A mixture of N,N-dimethyloctylamine (31.4 g.), 4-fluoro-carbanilino-chloromethane (37.5 g.) and acetone (100 cc.) is heated under reflux with stirring for 2 hours. On cooling to 5° C, a precipitate appears which is filtered off and dried at 50° C under reduced pressure. (4-Fluoro-carbanilinomethyl)-octyl-dimethylammonium chloride (52 g.) is thus obtained as a white powder which melts at 136° C.

The same final product is obtained by working as above, but in the absence of acetone.

The starting N,N-dimethylactylamine can be prepared in a similar manner to that described in Example 1 for N,N-dimethylheptylamine.

EXAMPLE 3

A mixture of 4-fluoro-carbanilino-chloromethane (24.4 g.), N,N-dimethyl-(2-ethyl-hexyl)-amine (20.4 g.) and methyl ethyl ketone (50 cc.) is heated under reflux with stirring for 4½ hours. The reaction mixture is cooled to about 20° C and stirred for 14 hours. The precipitate which has appeared is filtered of and dried at 50° C under reduced pressure. (4-Fluoro-carbanilino-methyl)-(2-ethylhexyl)-dimethylammonium chloride (38 g.) is thus obtained as a white powder which melts at 140° C.

The starting N,N-dimethyl-(2-ethyl-hexy)-amine can be prepared in a manner similar to that described in Example 1 for N,N-dimethylheptylamine.

EXAMPLE 4

A mixture of 4-fluoro-carbanilino-chloromethane (31.25 g.) and N,N-dimethyldecylamine (30.87 g.) is stirred for 1½ hours. The temperature of the reaction mixture, which is initially about 20° C, rises spontaneously and gradually to 50°–55° C and the mixture sets solid at the end of the stirring. After grinding the solid, (4-fluoro-carbanilino-methyl)-decyl-dimethylammonium chloride (62 g.) is obtained as a white powder which melts at 50° C.

The starting N,N-dimethyldecylamine can be prepared in a manner similar to that described in Example 1 for N,N-dimethylhepthylamine.

EXAMPLE 5

A mixture of 4-fluoro-carbanilino-chloromethane (19.7 g.), N,N-dimethyldecylamine (20.6 g.) and butyl ether (100 cc.) is stired at a temperature of 45°–50° C. After being heated for 1 hour, the mixture becomes oily and after 2 hours a precipitate gradually appears. Heating is maintained for a total of 4 hours and the reaction mixture is then cooled to about 20° C. The precipitate is filtered off, washed twice with hexane (a total of 120 cc.) and then dried first at 40° C and then at 50° C under reduced pressure. (4-Fluoro-carbanilino-methyl)-decyl-dimethylammonium. chloride (37.1 g.) is thus obtained as a white powder which melts at 112° C. The difference in the melting point compared with the product of the preceding Example can be explained by the fact that the product has crystallised better.

EXAMPLE 6

A mixture of 4-fluoro-carbanilino-chloromethane (48.2 g.) and N,N-dimethyllaurylamine (57.5 g.) is heated at 120° C, with stirring, for 9½ hours. Acetone (500 cc.) is added to the cooled reaction mixture and the mixture is then heated until the solid has dissolved completely. The solution obtained is cooled and the precipitate which has appeared is filtered of and dried at 40° C under reduced pressure. (4-Fluoro-carbanilino-methyl)-dodecyl-dimethylammonium chloride (20 g.) is thus obtained as a white powder which melts at 95° C.

The same final product is obtained by working without a solvent and at a temperature of between 20° and 50° C.

The starting N,N-dimethyllaurylamino can be prepared in a manner similar to that described in Example 1 for N,N-dimethylhepthylamine.

EXAMPLE 7

A mixture of 4-fluoro-carbanilino-chloromethane (15.6 g.) and N,N-dimethyltetradecylamine (21.2 g.) is heated at 120° C, with stirring, for 9 hours. The reaction mixture is dissolved in the minimum amount of hot acetone; the solution is cooled to about 20° C; the precipitate which has appeared is filtered off and dried at 50° C under reduced pressure. (4-Fluoro-carbanilino-methyl)-tetradecyl-dimethylammonium chloride (25 g.) is thus obtained as a white powder which melts at 115° C.

EXAMPLE 8

A solution of sodium bromide dihydrate (8.7 g.) in water (30 cc.) is added, over the course of 1 hour, to the soluton obtained by heating, at 50°–55° C, with stirring, a mixture of (4-fluorocarbanilino-methyl)-decyl-dimethyl-ammonium chloride (5.8 g.) and water (80 cc.). After the end of the addition, the reaction mixture is stirred at 50°–55° C for 2 hours and then dichloroethane (60 cc.) is added to it, the stirring being continued and the temperature being maintained at 50°–55° C for 15 minutes. The organic phase is isolated washed 4 times with water (a total of 240 cc.), and then concentrated to dryness under reduced pressure while the temperature is kept below 45° C. The residue is taken up in hexane (60 cc.), the crystals are filtered off, washed with hexane and dried at 50° C under reduced pressure. (4-Fluorocarbanilino-methyl)-decyl-dimethylammonium bromide (5.55 g.) is thus obtained as a white powder which melts at 110° C.

EXAMPLE 9

A mixture of 4-fluoro-carbanilino-bromomethane (14.8 g.), dimethyldecylamine (13.2 g.) and butyl ether (100 cc.) is heated at 45°–50° C, with stirring, for 4 hours. The precipitate which appears after cooling to about 20° C is filtered off, washed twice with hexane (a total of 100 cc.), and then dried at 50° C under reduced pressure. (4-Fluorocarbanilino-methyl)-decyl-dimethylammonium bromide (26 g.) is thus obtained as a white powder which melts at 112° C.

The starting 4-fluoro-carbanilino-bromomethane can be prepared in the following way: Thionyl chloride (63 g.) is added, with stirring and over the course of about 1 hours, to a mixture of bromoacetic acid (48.7 g.), dichloroethane (500 cc.) and a few drops of dimethylformamide, heated to 60° C. The reaction mixture is heated under reflux for 2 hours and then concentrated under reduced pressure to a residual volume of 100 cc. The Solution thus obtained is added, over the course of 1 hour, to a mixture of 4-fluoro-aniline (33.8 g.), dichloroethane (300 cc.) and sodium carbonate (36 g.) kept at a temperature below 35° C for the entire duration of the addition. The reaction mixture is then heated under reflux for 2 hours, and the inorganic salts which have precipitated are then filtered off. The organic filtrate is washed 4 times with water (a total of 1,600 cc.) at 70° C, and then cooled to 20° C. The precipitate which has appeared is filtered off and recrystallised from dichloroethane. After filtering off the crystals and drying them at 50° C under reduced pressure, 4-fluoro-carbanilino-bromomethane (40 g.) is obtained.

EXAMPLE 10

A solution of sodium iodide (9.7 g.) in water (30 cc.) is added over the course of 1 hour to the solution obtained by heating, at 50°–55° C, a mixture of (4-fluorocarbanilino-methyl)-decyl-dimethylammonium chloride (12 g.) and water (120 cc.). After the end of the addition, the reaction mixture is stirred at 50°–55° C for 2 hours and then dichloroethane (100 cc.) is added to it, stirring being continued and the temperature being maintained at 50°–55° C for 15 minutes. The organic phase is isolated, washed 3 times with water (a total of 300 cc.) and then concentrated to dryness under reduced pressure while the temperature is kept below 45° C. The solid yellow residue is taken up in hexane (60 cc.) and the crystals are filtered off and dried at 60° C under reduced pressure. (4-Fluorocarbanilinomethyl)-decyl-dimethylammonium iodide (12.8 g.) is thus obtained as a yellow powder which melts at 98° C.

EXAMPLE 11

A solution of sodium nitrate (4.1 g.) in water (20 cc.) is added over the course of 1 hour to the solution obtained by heating, at 50°–55° C, a mixture of (4-fluorocarbanilino-methyl)-decyl-dimethylammonium chloride (6 g.) and water (80 cc.) After the end of the addition, the reaction mixture is stirred at 50°–55° C for 2 hours, and then dichloroethane (60 cc.) is added to it, stirring being continued and the temperature being maintained at 50°–55° C for 15 minutes. The organic phase is isolated, washed 3 times with water (a total of 180 cc), and the concentrated to dryness under reduced pressure while the temperature is kept below 45° C. The oily residue obtained is triturated with hexane; the latter is removed by decanting; the residue is again triturated with hexane and this causes it to solidify almost completely; the hexane is again removed by decanting and the residue is dried under reduced pressure at about 20° C and then at 50° C. (4-Fluoro-carbanilino-methyl)-decyl-dimethyl-ammonium nitrate )6 g.) is thus obtained.

The compounds of formula (I) possess valuable germicidal properties; in particular, they are active against Gram-negative bacteria and more especially against Psuedomonas aeruginosa. They also possess good fungicidal power and a very low toxicity.

These various properties have been demonstrated in the following way:

Acute Toxicity

The acute toxicity of the products of Examples 4[(4-fluoro-carbanilino-methyl)-decyl-dimethyammonium chloride], 6 [(4-fluoro-carbanilino-methyl)-dodecyl-dimethylammonium chloride] and 7 [(4-fluorocarbanilino-methyl)-tetradecyl-dimethyammonium chloride] was compared, in mice, by subcutaneous administration, with that of two known disinfectant quaternary ammonium salts, namely benzalkonium chloride and cetrimonium bromide. The products were injected as a 4% strength aqueous solution and the number of deaths over the course of 7 days was observed. The results obtained were as follows:

| Product | Maximum dose which is always tolerated | Minimum dose which is always fatal | LD-50 |
| --- | --- | --- | --- |
| of Example 4. | 1,000 mg/kg | No deaths | >1,000 mg/kg |
| of Example 6. | 1,000 mg/kg | No deaths | >1,000 mg/kg |
| of Example 7. | 1,000 mg/kg | No deaths | >1,000 mg/kg |
| Benzalkonium chloride | 50 mg/kg | 80 mg/kg | 65 mg/kg |
| Cetrimonium bromide | 100 mg/kg | 250 mg/kg | 135 mg/kg |

Local Tolerance — Ocular Instillation

The daily instillation, over a period of 8 days, of a solution containing 1/4,000 of the above products did not cause any irritation.

Local Tolerance — Cutaneous Application

Solutions containing 2/1,000 of the above products were applied daily, over a period of 15 days, to the skin of the back, from which the hair had previously been removed, of groups of rats, at the same time brushing (two strokes in one direction and two strokes in the reverse direction) with a nylon brush. The rats thus treated did not show any irritation.

These experiments show that the local tolerance of the products of the invention is as good as for the two reference products.

Bacteriostatic Properties

They were determined by the usual methods, by successive dilution in an agar medium, against 23 species of bacteria, consisting of 8 Gram-positive bacteria:
Bacillus Subtilis (spores) ATCC 6633
Bactillus cereus (spores) ATCC 9634
Streptococcus faecalis ATCC 9854
Sarcine lutea ATCC 9341
Corynebacterium xerose CIP 5216
Staphylococcus aureus ATCC 6538 P
Staphylococcus aureus No. 1057
Staphylococcus aureus No. 1086
and 15 Gram-negative bacteria:
Salmonella typhi
Shigella sonnei
Escherichia coli
Escherichia coli 111B$_4$
Klebsiella pneumoniae
Enterobacter aerogenes
Serratia marcescens
Proteus rettgeri
Providencia
Pseudomonas aeruginosa ATCC 9027
Pseudomonas aeruginosa Haut.
Pseudomonas aeruginosa Pon.
Pseudomonas aeruginosa Mou.
Moraxella glucidolytica var. non liq.
Moraxella lwoffi var. liq Against the Gram-positive bacteria, the inhibitory dose of the products of Examples 4 6 and 7 is less than 10 μg/ml. Against the Gram-negative bacteria, the products of Examples 4 and 6 have an inhibitory effect at a concentration of less than 100 μg/ml and that of Example 7 has an inhibitory effect at a concentration of less than 100 μg/ml in the majority of cases and less than 1,000 μg/ml for a few strains.

By way of comparison, hexachlorophene displays an inhibitory effect at less than 10 μg/ml against Gram-positive bacteria, but has no effect against Gram-negative bacteria at less than 1,000 μg/ml.

Bactericidal Properties

They were investigated more particularly against Pseudomonas aeruginose (ATCC 9027) because of the proved resistance of this bacterium towards a large number of disinfectants.

Using known bacteriological technique, the experiment is carried out by removing the bacteria from the effect of the bactericides after a particular number of minutes, namely 1, 2, 5, 30 or 60 minutes. The number of surviving germs is determined, as a percentage. The bactericidal activity is considered to be good when not more than 0.1% of surviving germs remain.

After one minute of contact, a dose of 250 μg/ml of the product of Example 4, or a dose of 500 μg/ml of the product of Example 6, leaves less than 0.01% of surviving germs. By comparison the bactericidal doses, (based on 100% pure product) of the two known quaternary ammonium salts which are employed especially for medical use are 1,000 μg/ml and 1,500 μg/ml respectively.

Fungicidal Power

It is determined in known manner, by the dilution techniques in a Sabouraud medium.

The fungicidal activity of the products was determined on the following two strains: Aspergillus niger: a ubiquitous fungus, and Trichophyton mentagrophytes: a dermatophyte.

The fungicidal doses found were as follows:

| | Aspergillus niger | Tricophyton mentagrophytes |
| --- | --- | --- |
| Product of Example 2 | 1,000 μg/ml | 1,000 μg/ml |
| Product of Example 3 | 4,000 μg/ml | 4,000 μg/ml |
| Product of Example 4 | 500 μg/ml | 250 μg/ml |
| Product of Example 7 | 4,000 μg/ml | 4,000 μg/ml |

These properties of the compounds of the invention make them suitable for use as disinfectants for both industrial and medical use.

As disinfectants for industrial use, they can be employed in domestic hygiene for disinfecting crockery, sanitary equipment and floors, in laundering for disinfecting linen, and particularly hospital linen and babies' napkins, in the foodstuffs industry for disinfecting containers, utensils and equipment in general, and in the textile industry for preventing attacks by fungi.

For disinfecting linen and treating textiles, it is generally preferred to use the compounds of formula (I)

which have a low solubility in water, which possess a certain substantivity with respect to textiles, which makes residual disinfecting possible.

The disinfectant, bacteriostatic, bactericidal, fungicidal, and in general terms, germicidal compositions for general use which contain, as the active agent, at least one compound of formula (I) thus form a further subject of the present invention. These compositions can be solid or liquid. Powders or granules are examples of solid compositions. In these compositions, the active compound of the invention is mixed with one or more compatible inert diluents and optionally with substances other than diluents, for example, wetting agents and detergents compatible with the compounds of formula (I). Compositions of this type are very particularly suitable for disinfecting sanitary equipment. They can also be used, after being dissolved in water, for other uses.

Liquid compositions may be dilute or concentrated solutions or suspensions containing inert diluents and substances other than diluents for example wetting agents, detergents of flavouring substances compatible with the compounds of formula (I). The concentrated liquid compositions can be diluted with water at the time of use. Such liquid compositions are particularly suitable for domestic use, treating textiles and disinfecting floors.

These solid or liquid disinfectant compositions can optionally contain one or more other disinfectants compatible with the compounds of formula (I) and the diluents and adjuvants.

The following Examples illustrate disinfectant compositions for general use according to the invention.

EXAMPLE A

A powder having the following composition is prepared in known manner:

| | |
|---|---|
| (4-Fluoro-carbanilino-methyl)-decyl-dimethylammonium chloride | 50 g |
| Ethoxylated nonylphenol | 75 g |
| Anhydrous sodium carbonate | 200 g |
| Trisodium phosphate | 100 g |
| Tetrasodium pyrophosphate | 575 g |

The composition obtained can be used directly for disinfecting sanitary equipment.

EXAMPLE B

A powder having the following composition is prepared in known manner:

| | |
|---|---|
| (4-Fluoro-carbanilino-methyl)-decyl-dimethylammonium chloride | 30 g |
| Ethoxylated nonylphenol | 50 g |
| Anhydrous sodium carbonate | 450 g |
| Sodium bicarbonate | 470 g |

Ths composition can be dissolved in the water at the rate of 50 to 300 g. per 100 litres of water for use as a disinfectant in the milk industry.

EXAMPLE C

A solution having the following composition is prepared in known manner:

| | |
|---|---|
| (4-Fluoro-carbanilino-methyl)-decyl-dimethylammonium chloride | 50 g |
| Ethoxylated nonylphenol | 200 g |
| Distilled water | to 1,000cc |

By diluting 1 to 3 cc of this concentrated solution of 1 litre, a solution is obtained which can be used in domestic hygiene, for example disinfecting crockery.

As disinfectants for medical or surgical use, the compounds of formula (I) can be used for disinfecting wounds and burns, in the treatment of infected dermatoses, mycoses and ulcerations, for disinfecting operative fields, in gynaecology for treating vulvo-vaginal affections, in ophthalmology as an antiseptic in eye-washes, and for rinsing the hands of medical personnel.

The pharmaceutical compositions which can be used in therapy and which contain, as active ingredient, at least one compound of formula (I), constitute a further subject of the invention. These compositions can be liquids or creams in which the compounds of formula (I) are dissolved or dispersed in compatible excipients such as polyglycols or fatty alcohols. These compositions can also contain substances other than the diluents, for example flavouring agents which are compatible with the compounds of formula (I).

These compositions are used for external application and, depending on the degree of infestation of the patient to be treated, the doctor will decide the appropriate frequency of application.

The following Example illustrates pharmaceutical compositions according to the invention.

EXAMPLE A

A solution having the following composition is prepared in known manner:

| | |
|---|---|
| (4-Fluoro-carbanilino-methyl)-decyl-dimethylammonium chloride | 0.25 g |
| 70% strength ethyl alcohol | to 100 cc |

This solution may be used for disinfecting small wounds, cuts and burns, and for disinfecting operative fields.

We claim:

1. A method of killing or preventing the growth of Gram-negative bacteria which comprises contacting said bacteria with an amount of a quaternary ammonium compound of the formula:

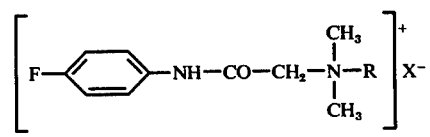

in which R is straight or branched alkyl of 7 to 16 carbon atoms and X⁻ is a monovalent anion, sufficient to kill or prevent the growth of said bacteria.

2. The method according to claim 1 in which in the said compound the anion X⁻ is the chloride, bromide, iodide or methosulphate ion.

3. The method according to claim 1 in which in the said compound R is n-heptyl, n-octyl, 2-ethyl-hexyl, n-decyl, n-dodecyl, n-tetradecyl or n-hexadecyl.

4. The method according to claim 1 in which the said compound is (4-fluoro-carbanilino-methyl)-heptyl-dimethyl-ammonium chloride.

5. The method according to claim 1 in which the said compound is (4-fluoro-carbanilino-methyl)-n-octyl-dimethylammonium chloride.

6. The method according to claim 1 in which the said compound is (4-fluoro-carbanilino-methyl)-(2-ethylhexyl)dimethylammonium chloride.

7. The method according to claim 1 in which the said compound is (4-fluoro-carbanilino-methyl)-n-decyl-dimethylammonium chloride.

8. The method according to claim 1 in which the said compound is (4-fluoro-carbanilino-methyl)-n-dodecyl-dimethylammonium chloride.

9. The method according to claim 1 in which the said compound is (4-fluoro-carbanilino-methyl)-n-tetradecyl-dimethylammonium chloride.

10. The method according to claim 1 in which the said compound is (4-fluoro-carbanilino-methyl)-n-decyl-dimethylammonium bromide.

11. The method according to claim 1 in which the said compound is (4-fluoro-carbanilino-methyl)-n-decyl-dimethylammonium iodide.

12. The method according to claim 1 in which the said compound is (4-fluoro-carbanilino-methyl)-n-decyl-dimethylammonium nitrate.

13. The method according to claim 1 in which the said bacteria are *Pseudomonas aeruginosa*.

* * * * *